United States Patent
An et al.

(10) Patent No.: US 9,993,171 B2
(45) Date of Patent: Jun. 12, 2018

(54) AUTOMATED SCREENING METHODS AND APPARATUSES FOR IMPLANTABLE MEDICAL DEVICES

(71) Applicant: CAMERON HEALTH INC., St. Paul, MN (US)

(72) Inventors: Qi An, Blaine, MN (US); Krzysztof Z. Siejko, Maple Grove, MN (US); Deepa Mahajan, Roseville, MN (US)

(73) Assignee: CAMERON HEALTH, INC., St. Paul, MN (US)

( * ) Notice: Subject to any disclaimer, the term of this patent is extended or adjusted under 35 U.S.C. 154(b) by 0 days. days.

(21) Appl. No.: 15/001,976

(22) Filed: Jan. 20, 2016

(65) Prior Publication Data

US 2016/0296131 A1    Oct. 13, 2016

Related U.S. Application Data

(60) Provisional application No. 62/144,755, filed on Apr. 8, 2015.

(51) Int. Cl.
| | |
|---|---|
| *A61B 5/02* | (2006.01) |
| *A61B 5/0402* | (2006.01) |
| *A61B 5/04* | (2006.01) |
| *A61B 7/02* | (2006.01) |
| *A61B 5/021* | (2006.01) |
| *A61B 5/1455* | (2006.01) |

(Continued)

(52) U.S. Cl.
CPC ........ *A61B 5/0402* (2013.01); *A61B 5/04011* (2013.01); *A61B 5/04012* (2013.01); *A61B 7/02* (2013.01); *A61B 5/021* (2013.01); *A61B 5/025* (2013.01); *A61B 5/0456* (2013.01); *A61B 5/0472* (2013.01); *A61B 5/14551* (2013.01); *A61B 5/4848* (2013.01); *A61B 7/00* (2013.01); *A61B 2505/05* (2013.01); *A61B 2560/0223* (2013.01)

(58) Field of Classification Search
USPC .................................................. 600/509–510
See application file for complete search history.

(56) References Cited

U.S. PATENT DOCUMENTS

| | | |
|---|---|---|
| 5,658,317 A | 8/1997 | Haefner et al. |
| 5,709,215 A | 1/1998 | Perttu et al. |

(Continued)

OTHER PUBLICATIONS

International Preliminary Report on Patentability, International Application No. PCT/US2008/074118, dated Feb. 24, 2010.

*Primary Examiner* — Nicole F Johnson
(74) *Attorney, Agent, or Firm* — Seager, Tufte & Wickhem LLP

(57) ABSTRACT

Automated pre-implant screening for candidate recipients of implantable medical devices. A set of cutaneous electrodes placed on a patient transcutaneously capture a cardiac signal using a screening device coupled to the electrodes. A first beat rate may be determined by identifying individual R-waves, QRS complexes or cardiac cycles from the captured cardiac signal using the cutaneous electrodes. A second beat rate may be calculated using one of several different methods, for example, by optical measurement, by monitoring heart sounds, by a second electric cardiac signal analysis, or by using an implanted device. The rates are compared to one another and, if a match is identified, the patient is deemed well suited to receive a particular device.

13 Claims, 11 Drawing Sheets

(51) Int. Cl.
    *A61B 5/025*     (2006.01)
    *A61B 5/0456*     (2006.01)
    *A61B 5/0472*     (2006.01)
    *A61B 5/00*     (2006.01)
    *A61B 7/00*     (2006.01)

(56) References Cited

U.S. PATENT DOCUMENTS

| | | | |
|---|---|---|---|
| 6,496,715 B1 | 12/2002 | Lee et al. | |
| 6,647,292 B1 | 11/2003 | Bardy et al. | |
| 6,721,597 B1 | 4/2004 | Bardy et al. | |
| 7,149,575 B2 | 12/2006 | Ostroff et al. | |
| 7,194,302 B2 | 3/2007 | Bardy et al. | |
| 7,392,085 B2 | 6/2008 | Warren et al. | |
| 7,623,909 B2 | 11/2009 | Sanghera et al. | |
| 7,655,014 B2 | 2/2010 | Ko et al. | |
| 8,079,959 B2 | 12/2011 | Sanghera et al. | |
| 8,200,341 B2 | 6/2012 | Sanghera et al. | |
| 8,483,841 B2 | 6/2013 | Sanghera et al. | |
| 8,565,878 B2 | 10/2013 | Allavatam et al. | |
| 8,588,895 B2 | 11/2013 | Sanghera et al. | |
| 8,909,331 B2 | 12/2014 | Sanghera et al. | |
| 2007/0123947 A1 | 5/2007 | Wenger et al. | |
| 2009/0054796 A1* | 2/2009 | Sanghera | A61B 5/04023 600/509 |
| 2011/0082378 A1* | 4/2011 | Messier | A61B 5/0002 600/509 |
| 2014/0275827 A1* | 9/2014 | Gill | A61B 5/4848 600/301 |
| 2014/0330327 A1 | 11/2014 | Thompson-Nauman et al. | |
| 2016/0045131 A1 | 2/2016 | Siejko | |
| 2016/0045132 A1 | 2/2016 | Siejko | |
| 2016/0045136 A1 | 2/2016 | Siejko et al. | |

\* cited by examiner

AUTOMATED SCREENING METHODS AND APPARATUSES FOR IMPLANTABLE MEDICAL DEVICES

CROSS REFERENCE TO RELATED APPLICATIONS

The present application claims the benefit of and priority to U.S. Provisional Application No. 62/144,755, filed Apr. 8, 2015, the disclosure of which is incorporated herein by reference.

BACKGROUND

Implantable devices such as implantable defibrillators can be beneficially used to automatically detect malignant arrhythmias in patient cardiac function and deliver appropriate therapy. There are known indicators for determining whether a patient is susceptible to arrhythmias, and whether the patient is therefore likely to benefit from receiving an implantable cardiac stimulation device. For example, measurements of ejection fraction coupled with patient history can be used to determine whether a patient may benefit from implantation of an implantable cardiac stimulus device (ICSD). Having identified a patient who needs an ICSD, the next step is to determine which of several ICSD options best suits the patient's needs. Tools for identifying patients who are well suited to certain ICSDs are desired. Additional alternatives and options are desired.

Overview

The present inventors have recognized, among other things, that a problem to be solved is the automation of screening of patients for certain implantable medical devices. For example, the S-ICD System, a subcutaneous implantable defibrillator available from Boston Scientific Corporation through its subsidiary Cameron Health, Inc., as originally introduced included a pre-screening tool which calls for an ECG to be captured, printed, and compared to shapes printed on a clear plastic screening tool. The process can be time consuming.

A first automated screening example includes applying a set of cutaneous electrodes on a patient to transcutaneously capture a cardiac signal using a screening device coupled to the electrodes. A first beat rate for one or more pairs of the applied electrodes is calculated using a first method, and can then be compared to a second beat rate calculated by second method. The second method may also use the cutaneous electrodes or may use a different signal. The first beat rate may be determined by identifying individual R-waves, QRS complexes or cardiac cycles from the captured cardiac signal using the cutaneous electrodes. The second beat rate may be calculated using one of several different methods, for example, by optical measurement, by monitoring heart sounds, or by a second electric signal analysis, using an implanted device. The first and second beat rates can then be compared to determine suitability of the patient for receiving the implantable device for which screening is performed.

A first illustrative example takes the form of a screening device configured to perform patient screening to determine whether a patient is well suited to receiving a first implantable medical device (IMD) comprising: a user interface; an port configured to receive signals from at least surface electrodes for cutaneous placement on a patient; and operational circuitry configured to receive signals from the port and perform a patient screening method, and to use the user interface to provide information and/or instructions to a user and receive inputs therefrom. In the first illustrative example, the operational circuitry may comprise first rate calculation means for calculating a first cardiac rate using signals from the surface electrodes by a first analysis, second rate calculation means for obtaining a second cardiac rate by a second analysis; wherein the second analysis is different from the first analysis; and comparing means for comparing the first cardiac rate to the second cardiac rate to determine whether the patient is well suited to receiving the first IMD if the first cardiac rate and the second cardiac rate match within predetermined bounds.

A second illustrative example takes the form of a screening device as in the first illustrative example, wherein the first rate calculation means is configured such that the first analysis is similar to an analysis which the first IMD would use to analyze cardiac signals. A third illustrative example takes the form of a screening device of either of the first two illustrative examples wherein the comparing means is configured to provide an output via the user interface indicating that the patient is not well suited to receiving the IMD if the first and second rates do not match.

A fourth illustrative example takes the form of a screening device as in any of the first three illustrative examples, wherein the first analysis comprises a beat detection method for detecting individual heartbeats by comparison of a signal to a detection threshold, and the second analysis comprises comparing a segment of a signal received from the surface electrodes to itself at varying degrees of temporal offset to identify a periodicity of the signal. A fifth illustrative example takes the form of a screening device as in any of the first three illustrative examples, wherein the first analysis comprises a beat detection method for detecting individual heartbeats by comparison of a signal to a detection threshold, and the second analysis comprises obtaining a heart rate from a blood pressure monitoring system communicatively coupled to the screening device. A sixth illustrative example takes the form of a screening device as in any of the first three illustrative examples, wherein the first analysis comprises a beat detection method for detecting individual heartbeats by comparison of a signal to a detection threshold, and the second analysis comprises obtaining a heart rate by the use of a pulse oximeter communicatively coupled to the screening device.

A seventh illustrative example takes the form of a screening device as in any of the first three illustrative examples, wherein the first analysis comprises a beat detection method for detecting individual heartbeats by comparison of a signal to a detection threshold, and the second analysis comprises obtaining a heart rate by interrogation of an already implanted cardiac management or monitoring system communicatively coupled to the screening device in the patient. An eighth illustrative example takes the form of a screening device as in any of the first three illustrative examples, wherein the first analysis comprises a beat detection method for detecting individual heartbeats by comparison of a signal to a detection threshold, and the second analysis comprises obtaining a heart rate by monitoring heart sounds.

A ninth illustrative example takes the form of a screening device as in any of the first eight illustrative examples, which is configured to output, via the user interface, a desired posture for the patient to assume during a first assessment by the first and second rate calculation means and which, upon completion of analysis by the first and second rate calculation means, is configured to output, via the user interface, a second desired posture for the patient to assume during a second assessment by the first and second rate calculation means. A tenth illustrative example takes the form of the ninth illustrative example, wherein the first posture is seated and the second posture is laying down. An eleventh illustrative example takes the form of the ninth illustrative example wherein the first posture is seated and the second posture is prone.

A twelfth illustrative example takes the form of a screening device as in any of the first eleven illustrative examples, further configured to indicate, via the user interface, that the patient is to be exercising during a first assessment by the first and second rate calculation means.

A thirteenth illustrative example takes the form of a system comprising a screening device as in any of the first twelve illustrative examples further comprising a plurality of cutaneous electrodes configured to couple to the input port of the device. A fourteenth illustrative example takes the form of a system as in the thirteenth illustrative example, wherein the operational circuitry further comprises selection means for selecting a subset of the cutaneous electrodes for use in analysis by the first and second rate calculation means. A fifteenth illustrative example takes the form of a system as in the fourteenth illustrative example, wherein the selection means is configured to select a subset of the cutaneous electrodes for a first iteration of patient assessment by the first and second rate calculation means and a second subset of the cutaneous electrodes for a second iteration of patient assessment by the first and second rate calculation means, to check whether the patient is well suited for receiving the first IMD in light of analysis of each of at least first and second subsets of the cutaneous electrodes.

A sixteenth illustrative example takes the form of a method of determining whether an implantable device is appropriate for a patient comprising sensing cardiac signals by applying a plurality of cutaneous electrodes to a patient and receiving electrical signals therefrom, analyzing a first cardiac signal using a first method for generating a heart rate to yield a first rate, using a second method for generating a heart rate to yield a second heart rate, wherein the first and second methods are distinct from one another, determining whether the first rate and second rate match using predefined parameters for finding a match, and, if so, determining that the implantable device is appropriate for the patient. A seventeenth illustrative example takes the form of a method as in the sixteenth illustrative example, further comprising, if the first rate and second rate do not match, performing manual screening of the patient.

An eighteenth illustrative example takes the form of a method as in either of the sixteenth or seventeenth illustrative examples, wherein the first cardiac signal is sensed between first and second cutaneous electrodes that define a first sensing vector, wherein if the first rate and the second rate do not match using the predefined parameters, the method further comprises sensing a second cardiac signal using a second sensing vector different from the first sensing vector, analyzing the second cardiac signal using the first method for generating a heart rate to yield a third rate, using the second method for generating a heart rate to yield a fourth rate, determining whether the third rate and fourth rate match using the predefined parameters for finding a match, and, if so, determining that the implantable device is appropriate for the patient. A nineteenth illustrative example takes the form of a method as in the eighteenth illustrative example, wherein the first cardiac signal and the second cardiac signal are captured at the same time.

A twentieth illustrative example takes the form of a method as in the sixteenth illustrative example, wherein the first cardiac signal is sensed between cutaneous electrodes that define a first sensing vector, wherein if the first rate and the second rate do not match using the predefined parameters, the method further comprises: analyzing a second cardiac signal using the first method for generating a heart rate to yield a third rate, the second cardiac signal being sensed between cutaneous electrodes that define a second sensing vector different from the first sensing vector, determining whether the third rate and second rate match using the predefined parameters for finding a match, and, if so, determining that the implantable device is appropriate for the patient. A twenty-first illustrative example takes the form of a method as in the twentieth illustrative example, wherein the second cardiac signal is sensed at the same time as the first cardiac signal.

A twenty-second illustrative example takes the form of a method as in the sixteenth illustrative example, wherein the first method for generating a heart rate comprises a beat detection method for detecting individual heartbeats by comparison of a cardiac electrical signal to a detection threshold, and the second method for generating a heart rate comprises comparing a segment of a signal to itself at varying degrees of temporal offset to identify a periodicity of the first cardiac signal and deriving a heart rate therefrom. A twenty-third illustrative example takes the form of a method as in the sixteenth illustrative example, wherein the first method for generating a heart rate comprises a beat detection method for detecting individual heartbeats by comparison of a cardiac electrical signal to a detection threshold, and the second method for generating a heart rate comprises the use of a blood pressure monitoring system. A twenty-fourth illustrative example takes the form of a method as in the sixteenth illustrative example, wherein the first method for generating a heart rate comprises a beat detection method for detecting individual heartbeats by comparison of a cardiac electrical signal to a detection threshold, and the second method for generating a heart rate comprises the use of heart sounds. A twenty-fifth illustrative example takes the form of a method as in the sixteenth illustrative example, wherein the first method for generating a heart rate comprises a beat detection method for detecting individual heartbeats by comparison of a cardiac electrical signal to a detection threshold, and the second method for generating a heart rate comprises the use of a pulse oximeter. A twenty-sixth illustrative example takes the form of a method as in the sixteenth illustrative example, wherein the first method for generating a heart rate comprises a beat detection method for detecting individual heartbeats by comparison of a cardiac electrical signal to a detection threshold, and the second method for generating a heart rate comprises interrogation of an already implanted cardiac management or monitoring system. A twenty-seventh illustrative example takes the form of a method as in any of the sixteenth to twenty-sixth illustrative examples, further comprising generating an output via the user interface to instruct the patient to adopt at least first and second postures for repeatedly determining the patient's suitability for receiving the implantable device through analysis of cardiac signals captured in at least the first and second postures.

A twenty-eighth illustrative example takes the form of a screening device configured to perform patient screening to determine whether a patient is well suited to receiving a first implantable medical device (IMD) comprising: a user interface, a port configured to receive signals from at least surface electrodes for cutaneous placement on a patient, and operational circuitry configured to receive signals from the port and perform a patient screening method, and to use the user interface to provide information and/or instructions to a user and receive inputs therefrom; wherein the operational circuitry is configured to: perform a first method of determining cardiac rate using signals from the surface electrodes to calculate a first cardiac rate, wherein the first method is similar to a method used by the first IMD to determine cardiac rate; obtain a second cardiac rate by a second method different from the first method; and compare the first cardiac rate to the second cardiac rate and determine whether the first cardiac rate and second cardiac rate are similar, and, if so, determine that the patient is well suited to receiving the first IMD.

A twenty-ninth illustrative example takes the form of a system comprising a device as in the twenty-eighth illustrative example and a plurality of cutaneous electrodes communicatively coupled to the port of the device, wherein the operational circuitry of the screening device is configured such that: the first cardiac rate is calculated using a first pair of the cutaneous electrodes that define a first sensing vector, if the first rate and the second rate do not match using the predefined parameters, the operational circuitry is configured to select a different pair of the cutaneous electrodes that define a second sensing vector and repeat the steps of calculating a first cardiac rate, this time using the second sensing vector in order to determine whether the second sensing vector yields a match of the first and second cardiac rates.

A thirtieth illustrative example takes the form of a screening device as in the twenty-eighth illustrative example wherein the operational circuitry is configured such that the first method for generating a heart rate comprises a beat detection method for detecting individual heartbeats by comparing a signal to a detection threshold, and the second method for generating a heart rate comprises comparing a segment of a signal to itself at varying degrees of temporal offset to identify a periodicity. A thirty-first illustrative example takes the form of a screening device as in the twenty-eighth illustrative example wherein the operational circuitry is configured such that the first method for generating a heart rate comprises a beat detection method for detecting individual heartbeats by comparing a signal to a detection threshold, and the second method for generating a heart rate comprises the use of a pressure monitoring system communicatively coupled to the screening device. A thirty-second illustrative example takes the form of a screening device as in the twenty-eighth illustrative example wherein the operational circuitry is configured such that the first method for generating a heart rate comprises a beat detection method for detecting individual heartbeats by comparing a signal to a detection threshold, and the second method for generating a heart rate comprises the use of a pulse oximeter communicatively coupled to the screening device.

A thirty-third illustrative example takes the form of a screening device as in the twenty-eighth illustrative example wherein the operational circuitry is configured such that the first method for generating a heart rate comprises a beat detection method for detecting individual heartbeats by comparing a signal to a detection threshold, and the second method for generating a heart rate comprises interrogation of an already implanted cardiac management or monitoring system communicatively coupled to the screening device. A thirty-fourth illustrative example takes the form of a screening device as in the twenty-eighth illustrative example, wherein the operational circuitry is configured such that the first method for generating a heart rate comprises a beat detection method for detecting individual heartbeats by comparing a signal to a detection threshold, and the second method for generating a heart rate comprises the use of heart sounds.

A thirty-fifth illustrative example takes the form of an external device for use in assessing a patient's suitability for receiving an implantable cardiac device comprising: a user interface for providing instructions and information to and receiving inputs from a user; a first means for detecting cardiac rate, the first means providing a cardiac rate that is configured to emulate a cardiac rate that would be calculated by an implantable medical device; a second means for detecting cardiac rate, the second means providing a cardiac rate that is configured to be more accurate than the first means; and a controller for comparing the cardiac rates of the first and second means and directing the inputs and outputs of the user interface.

This overview is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

The following detailed description makes reference to the various parts of an electrocardiogram (ECG). An ECG includes several portions (often referenced as "waves") that, according to well-known convention, are labeled with letters including P, Q, R, S, and T, each of which corresponds to particular physiological events. Taken together, the Q, R and S waves can be referred to as the cardiac complex. Heart beats are cardiac cycles which include, generally in healthy patients, the set of P, Q, R, S, and T waves (there is also a U-wave but it is generally small enough to be unseen due to the T-wave). In many implantable cardiac pacemakers, defibrillators, heart failure devices, and diagnostic devices, cardiac cycles are counted relative to time to determine the beat rate for a patient. There are other approaches to identifying beat rate which are noted below. Obtaining an accurate beat rate allows therapeutic or diagnostic devices to perform most efficiently. In several embodiments of the present invention, the ability to accurately determine beat rate is prospectively analyzed to determine suitability of cardiac systems for particular patients.

Figure 1:
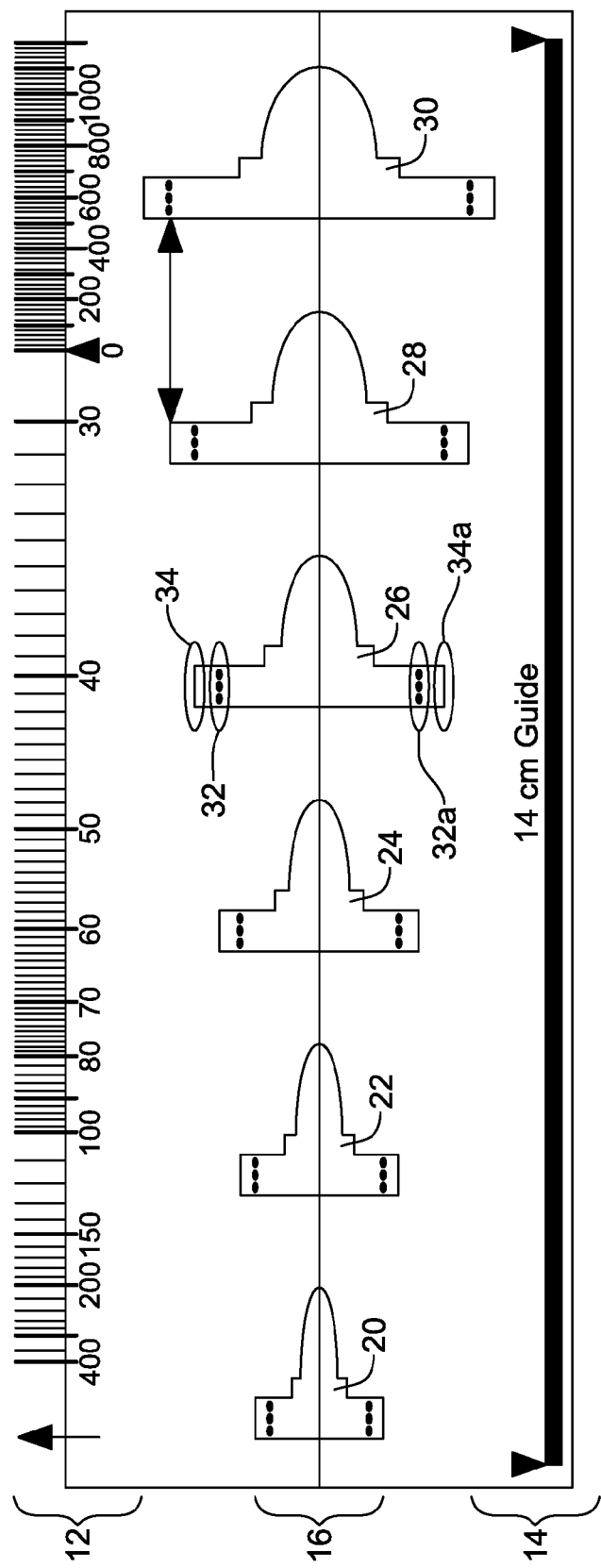
FIG. 1 illustrates a prior art pre-screening tool.

FIG. 1 shows an illustrative prior art example of a patient screening tool 10 which would be provided on a piece of clear, durable plastic, and which is intended for use with a printed ECG. The patient screening tool 10 includes a rate scale shown at 12. The rate scale 12 can be used to estimate the rate of a patient's ongoing cardiac rhythm by aligning a QRS complex from a printed ECG with the vertical arrow near the left edge of the rate scale 12 and determining where the next QRS complex to the right of the aligned QRS complex appears on the scale. In an example, a practitioner is instructed to perform patient screening when the patient's heart rate is in a predefined range, for example, less than 120 beats per minute (BPM), and to use a predetermined printing rate (such as 25 mm/sec) for printing the ECG.

A spacing guide is provided as shown at 14. The spacing guide 14 can be used to assist in the correct placement of cutaneous electrodes on the patient to correlate with electrode positions for the system the patient may receive. In the embodiment shown in FIG. 1, the screening tool is adapted for use with a subcutaneous-only ICSD similar to that shown in FIG. 2, below, and the spacing guide can be used to identify spacing along the patient's sternum.

The illustrative screening tool 10 also includes a stencil 16. The stencil 16 includes a number of shapes 20, 22, 24, 26, 28, 30 disposed along an alignment line shown across the center of the patient screening tool 10. Though not shown in FIG. 1, the individual shapes in the prior art example are not only outlined, but each is uniquely colored. The shapes 20, 22, 24, 26, 28, 30 are sized such that each can be used for a particular range of ECG amplitudes, from smaller amplitudes (shape 20) to larger amplitudes (shape 30). To identify which shape to use, the dashed lines of each shape 20, 22, 24, 26, 28, 30 are used. For example, if the peak amplitude of an aligned QRS complex does not fall within spaces between dashed line 32 and outer boundary 34 or between 32A and 34A of shape 26, then shape 26 is not the right size for that QRS complex. Thus, the dashed lines provide amplitude guidelines for using the shapes 20, 22, 24, 26, 28, 30.

To determine whether a given patient is well suited to receive a particular ICSD, a correctly sized shape 20, 22, 24, 26, 28, 30 is compared to the printed ECG when it is aligned with a QRS complex. A QRS complex fails if the ECG trace crosses outside an appropriately sized shape 20, 22, 24, 26, 28, 30; otherwise, the QRS passes. A certain number of QRS complexes from the patient are checked against the tool 10; if the QRS complexes fail in a particular sensing vector, then that vector fails. If all vectors fail, then the patient is deemed to have failed pre-screening. If a vector passes, the patient may be asked to assume a different posture (going from sitting to standing or laying down, for example), or the patient may simply be found to have passed. Fuller discussion and details of the screening tool and variants thereon may be found in U.S. Pat. No. 8,079,959, the disclosure of which is incorporated herein by reference.

In response to screening, a decision is made whether to implant the particular ICSD in the configuration for which testing was performed, or to use a different therapy (a different ICSD or a different configuration of the same ICSD, for example). This approach using the screening tool 10 calls for time consuming assessment of printed ECG strips. Quicker and/or less cumbersome methods are desired.

Figure 2:
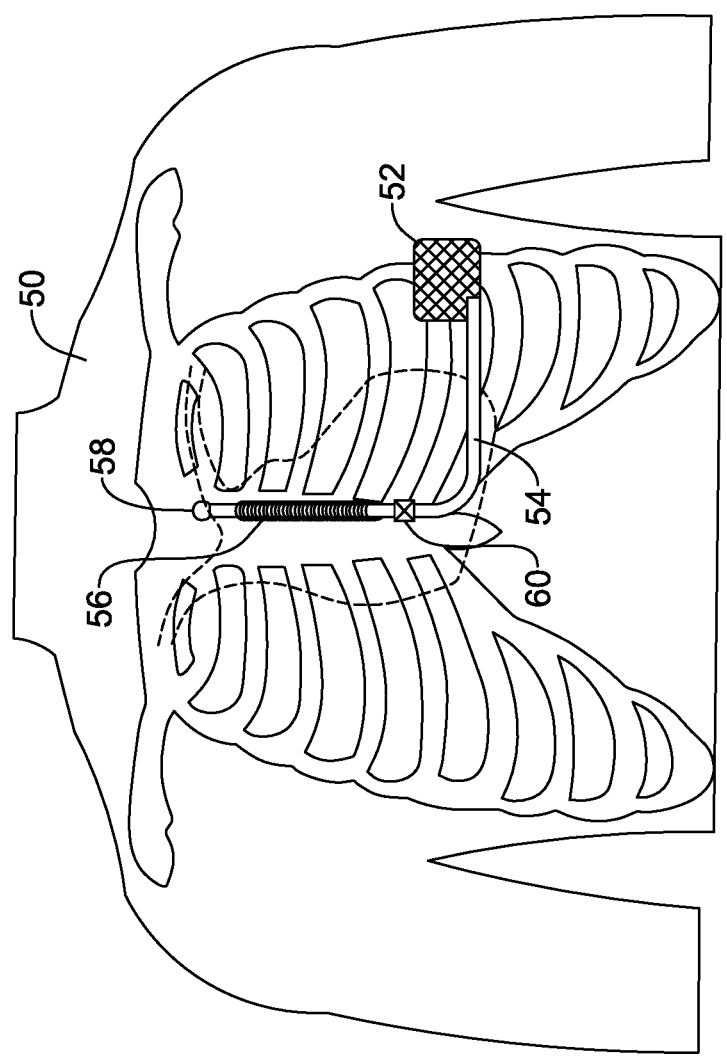
FIG. 2 illustrates a subcutaneous implantable cardioverter-defibrillator relative to a patient.

FIG. 2 illustrates a subcutaneous implantable cardioverter-defibrillator relative to a patient. The system shown generally corresponds to the S-ICD® System available from Boston Scientific Corporation and its subsidiary, Cameron Health, Inc. (as does the screening tool of FIG. 1). The system is shown implanted in a patient 50, for whom certain anatomical features are outlined including the ribcage and heart. The subcutaneous defibrillator includes a canister 52 implanted near the left axilla, about level with the inframammary crease, with a lead 54 extended medially toward the sternum and xiphoid of the patient 50. Near but just to the left of the sternum, the lead 54 is directed superiorly along the sternum. The lead 54 is shown having three electrodes including a coil electrode 56 and two smaller electrodes 58, 60 disposed along the left margin of the sternum. More or fewer electrodes may be provided and various functions can be performed using each electrode 56, 58, 60. Some examples of leads and electrode spacing are shown in U.S. Pat. No. 8,483,841, titled ELECTRODE SPACING IN A SUBCUTANEOUS IMPLANTABLE CARDIAC STIMULUS DEVICE, the disclosure of which is incorporated herein by reference, though other structural and spacing configurations may be used as well.

The implant location shown in FIG. 1 is merely illustrative of one of several locations that can be used for implantation of a subcutaneous defibrillator system. While this location is shown repeatedly in the later figures, it should be understood that other locations such as shown in U.S. Pat. Nos. 6,647,292, 6,721,597, 7,194,302, 7,149,575 and/or 7,655,014, which are incorporated herein by reference, may be used as well. While the present invention may be used for a screening system for an implantable product as shown by FIG. 2, other implantable products may be screened as well or instead of that shown. Rather than a subcutaneous device, a substernal approach such as in U.S. PG Publication No. 2014-0330327, the disclosure of which is incorporated herein by reference, may be used to place one or more of a defibrillation and/or pacing lead.

Several sensing vectors are made available by the system as shown in FIG. 2. For example, cardiac signals may be sensed between pairs of electrodes including pairs 52-56, 52-58, 52-60, 56-60, 56-58, and 58-60. Discussions of sensing vector usage and selection for a subcutaneous system can be found in U.S. Pat. Nos. 7,392,085, 7,623,909, and 8,200,341, for example, the disclosures of which are incorporated herein by reference. For an implantable device configured to have multiple available sensing vectors, prescreening may include a check of several analogous sensing vectors.

Figure 3:
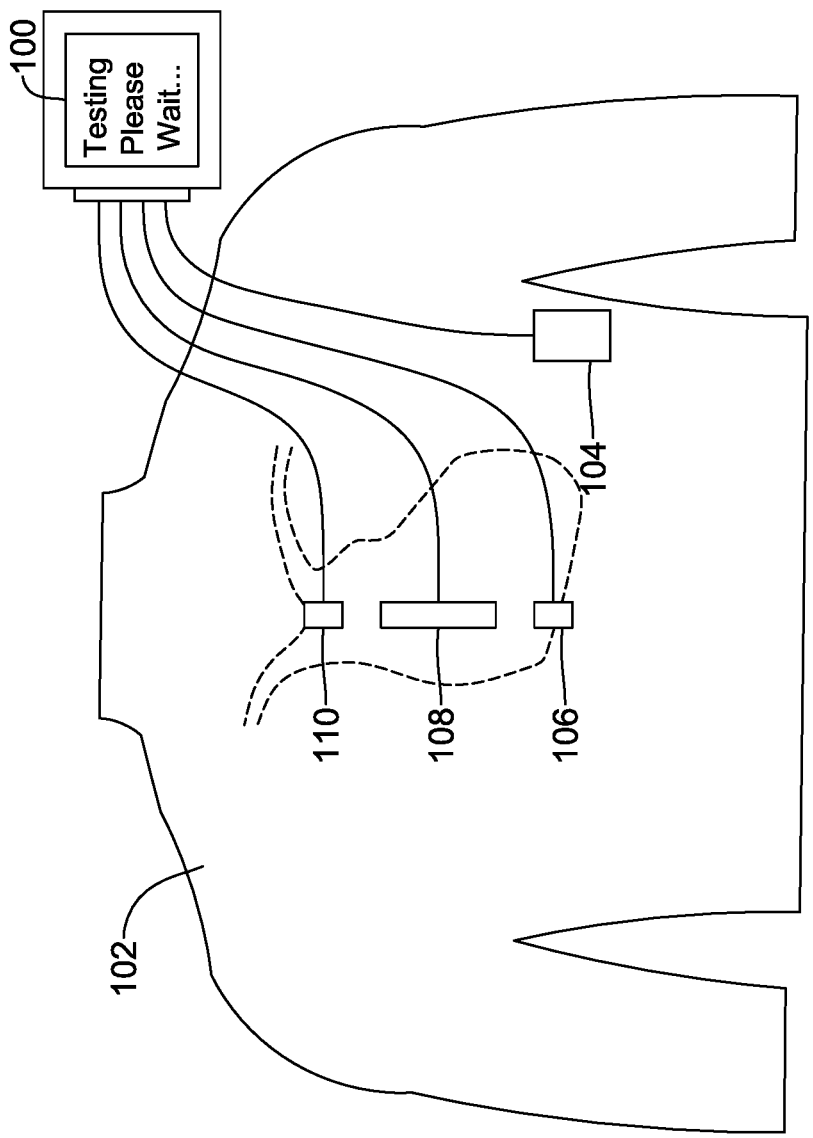
FIG. 3 illustrates an automated screening system for use with a system such as that shown in FIG. 2.

FIG. 3 illustrates an automated screening system for use with a system such as shown in FIG. 2. The screening system includes an external device 100 for screening the patient 102, which is coupled to surface electrodes 104, 106, 108, and 110. The surface electrodes 104, 106, 108, and 110 are shown placed in positions that would correspond to the implant locations for the canister 52 and electrodes 60, 56, and 58, respectively, of FIG. 2. In some examples, the coil electrode 56 (FIG. 2) is not used for sensing the subcutaneous defibrillator, and so corresponding surface electrode 108 may be omitted. As with the implantable system, multiple sensing vectors are defined among the surface electrodes 104, 106, 108, and 110. The positions/locations shown are merely illustrative of one embodiment, and other surface locations may be used.

The external device 100 may take the form of a handheld device such as a cell phone, or it may be a tablet or laptop computer, or may be a medical device such as a programmer configured for use with implantable systems or a specially designed patient screening device. The external device 100 may include operational circuitry that may contain input/output circuits, logic circuitry, memory devices, a processor or controller, batteries and other power supply circuitry, communication circuitry and any other suitable elements. While the external device 100 is shown with only a screen (which may be a touchscreen interface), additional elements such as a touchpad, keyboard, mouse, speakers, or other interface elements may be included, as well as communication circuitry or adaptors for coupling to internet or cellular networks. A printer may also be provided in association with the external device 100.

Rather than a subcutaneous device, a substernal approach such as in U.S. PG Publication No. 2014-0330327, the disclosure of which is incorporated herein by reference, may be used to place one or more of a defibrillation and/or pacing lead. If such a system is to be implanted or is an option, the surface electrodes 106, 108, 110 shown in FIG. 3 may simply be placed cutaneously over the intended/desired implant location of the substernal lead.

Figure 4:
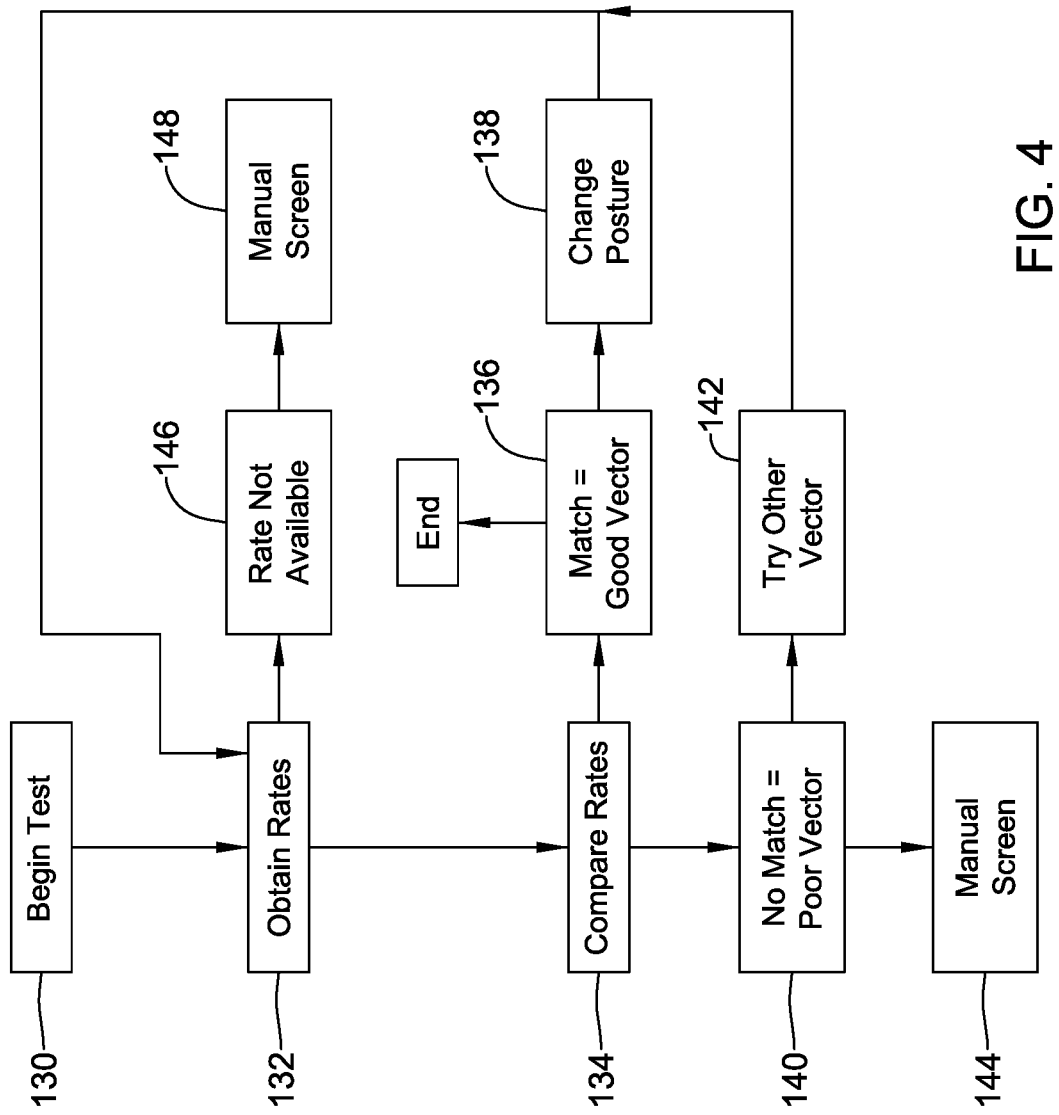
FIG. 4 is a flow diagram for an illustrative method of patient screening.

FIG. 4 is a flow chart for an illustrative method of patient screening. In the illustrative method, the test or screen begins at block 130. At least first and second rates of cardiac events are calculated. The first and second rates are calculated using distinct methods of cardiac rate calculation, in which at least one of the rates corresponds to a rate calculation method that is intended to be used in the implantable device for which screening is being performed. The other of the rates is preferably calculated using a different rate calculation algorithm.

For example, a first rate can be calculated using a surface ECG, while a second rate is calculated using a pulse oximeter, by monitoring variation in blood pressure, by a device sensing heart sounds, or by other patient external devices. In another example, both first and second rates may be calculated from a surface ECG, but with a first rate calculated using an R-wave detection method such as that shown in FIG. 5 below, and the second rate calculated using a self-correlation method as shown in FIGS. 6 and 7. In yet another example, a patient who already has an implanted cardiac device such as a transvenous pacemaker or defibrillator, an implantable cardiac monitor, or a leadless cardiac pacemaker, can undergo screening by calculating cardiac rate using a surface ECG as the first rate, and obtaining a detected rate from the already implanted cardiac device in block 132.

In an illustrative example, at least one of the first and second rates is a validated method corresponding to a method which would be used in an implantable device, operating using validated input hardware that mimics the amplification, filtering and sampling characteristics of the implantable device. In another example, there may be several rates calculated using validated methods corresponding to different devices or different variants of the same device, possibly using different input hardware and/or different digital handling of the incoming signals to mimic how the different devices or methods may amplify, filter and/or sample the incoming signals. For example, if first and second rate calculations are available within a single implantable device, both rate calculations may be used.

Figure 5:
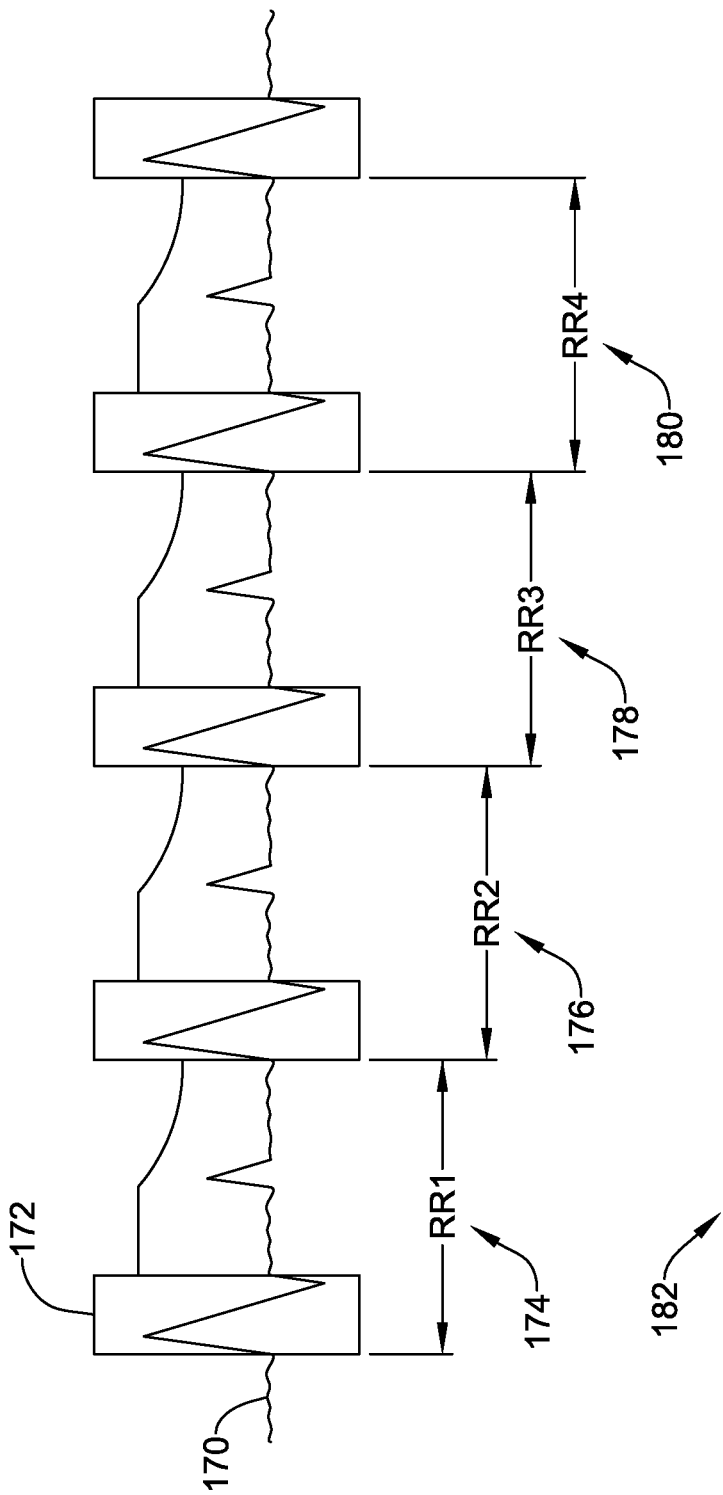
FIG. 5 illustrates, graphically, a first method of determining cardiac beat rate.
Figure 6:
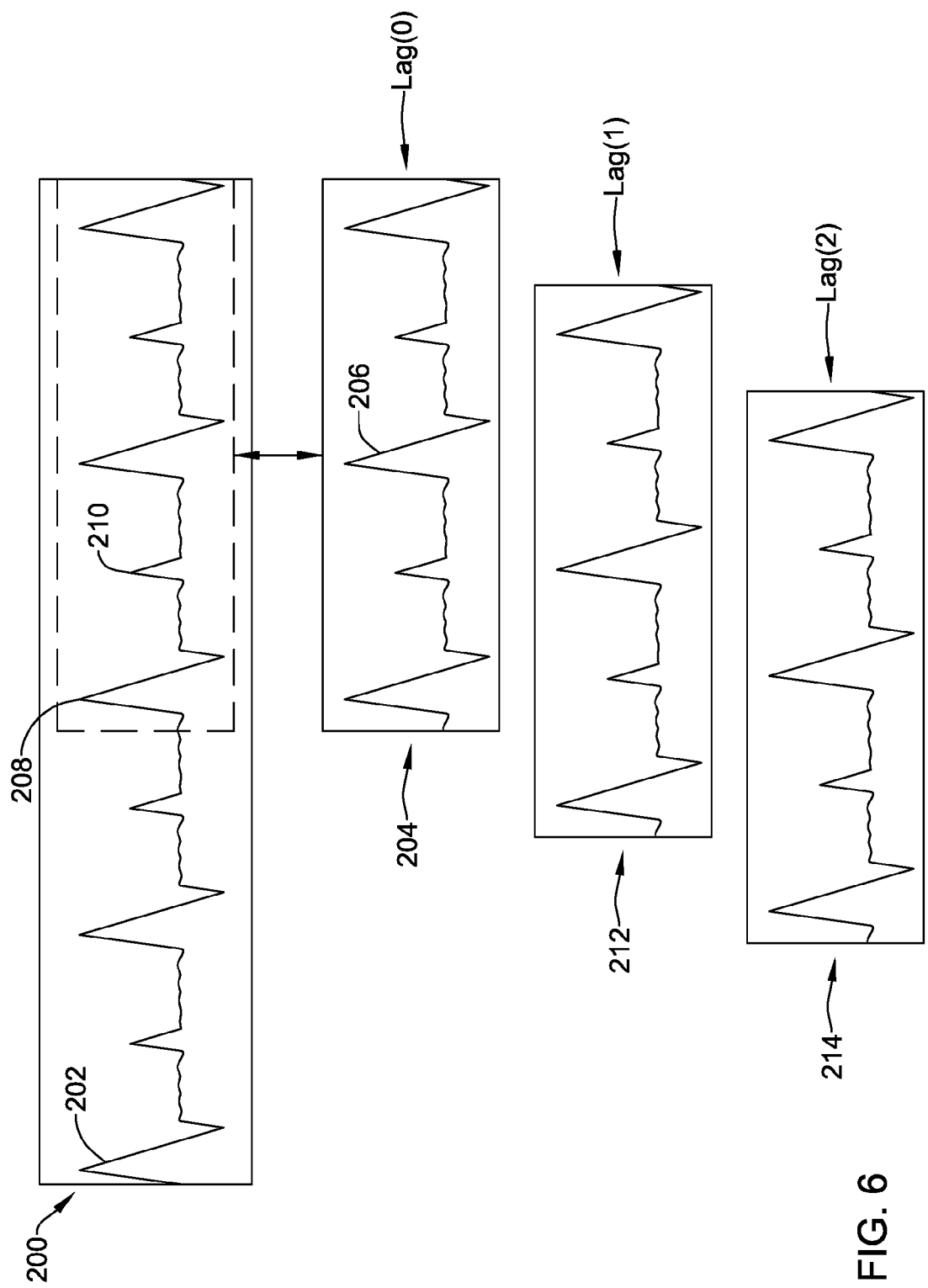
FIGS. 6 and 7 illustrate, graphically, a second method of determining cardiac beat rate.
Figure 7:
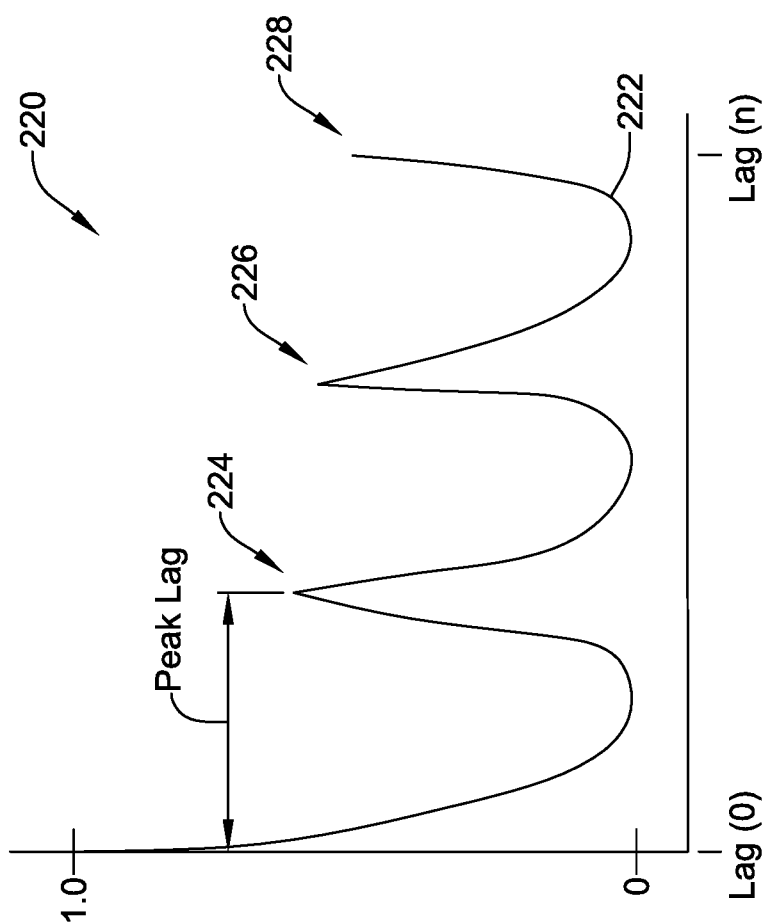

In some examples, each of the methods of FIG. 5 and FIGS. 6-7 are used along with a pulse oximeter, yielding three rate calculations. In a first such example, a proposed implantable device is configured to use either or both of the rate calculations shown in FIG. 5 and FIGS. 6-7. For this first such example, the pulse oximeter rate is compared against the other two rates to determine whether at least one method of rate calculation for the proposed implantable system is likely to be accurate. In a second such example, a first proposed implantable device is configured to use the method as in FIG. 5, while a second proposed implantable device is configured to use the method as in FIGS. 6-7, and comparison to the pulse oximetry rate is used to select between the first and second proposed implantable devices.

Once the at least first and second rates are obtained in block 132, the rates are compared to one another as indicated at 134. By comparing a rate that is captured in a manner that corresponds to the pre-screened implantable device against a second detected rate, it can be determined (at least by a first pass) whether reliable cardiac event rate can be detected—it is assumed to be unlikely that both the first and second rates could be wrong and match.

Rates may be considered to be a match using various criteria; a relatively simple approach would be to determine whether the first and second rates are within a predefined percentage (5 to 20%, for example) of one another. In one example, four to forty-five seconds of data are used, and the rates as calculated by each of the first and second method are required to stay within 10% of one another during the time period. If numerous rate calculations occur, statistical equivalence may be used—for example, if thirty seconds of data are used, the methods shown in FIGS. 5-7, below, could provide a dozen or more rate outputs each, and means and standard deviations for each could be calculated.

The first and second rate calculations may occur at the same time—that is the same heart beats may be detected by both methods. In an alternative, the first and second rate calculations may overlap in time, but need not necessarily use exactly the same data. The first and second rate calculations may in fact occur using entirely separate data, without overlapping, though it is preferred that there be at least some overlap so that a change in the patient's actual intrinsic cardiac rhythm may be ruled out as a source of mismatch.

In an alternative example, rather than comparing rates, if individual cardiac beats are being detected in each of first and second beat detection methods, the timing of individual detections may be compared. If a 1:1, stable timing relationship occurs it may be presumed that the first and second beat detection methods are both working well.

If the check at 134 yields matching rates, then a good sensing vector may be declared, as indicated at 136. As a result, the method would conclude that the patient is a good candidate to receive the screened medical device. Optionally, the patient may be requested to change posture, for example, by standing or sitting up rather than laying down (assuming the first set of rates were captured while the patient is laying down), as indicated at 138, and the rate capture 132 and comparison 134 can be repeated for the additional posture(s). Again, matches suggest a good vector and that the patient is a good candidate; mismatched outputs suggest the patient may be a poor candidate or requires further assessment.

If the rates do not match the method may declare a poor sensing vector, as indicated at 140. One or more other sensing vectors may be tested, as indicated at 142. If all available sensing vectors have been tested and fail, the proposed implantable system may be deemed poorly suited to the patient or, as shown at 144, a manual screening process using a tool such as shown above in FIG. 1 may be performed.

In some examples, data from all vectors may be captured at once allowing the entire screening to be performed in, for example, less than a minute if a single posture is used. A data capture may be performed to capture signals from plural vectors simultaneously, and the individual sensing vectors may be analyzed individually or in combinations to determine whether one or more sense vectors provide reliable rate calculations.

Returning briefly to block 132, if a cardiac rate cannot be calculated due to sensing difficulty, as indicated at 146, then either the proposed implantable system may be deemed poorly suited to the patient, or a manual screening process may be performed as shown at 148.

In some examples, the method of FIG. 4 is performed while the patient is at rest, laying, sitting or standing in a clinical setting. In other examples, the patient screening may be performed while the patient is asked to exercise. The use of exercise testing may reveal rate induced changes in the cardiac rhythm such as a bundle branch block, which can alter the accuracy of cardiac event detection in some circumstances.

FIG. 5 illustrates, graphically, a first method of determining cardiac beat rate. The method is shown graphically but it will be understood that the analysis can be implemented in software and performed automatically, without graphics being shown to anyone, in the external device 100, for example, of FIG. 3. The ECG is shown at 170. A detection profile is shown at 172. Each time the ECG crosses the detection profile 172, a beat is declared and a refractory period occurs, with the refractory period shown in cross hatching. There are various ways to perform beat detection that may be suitable for the present invention. Some examples can be found in U.S. Pat. Nos. 5,658,317, 5,709, 215, and 8,565,878, the disclosures of which are incorporated herein by reference.

It is presumed that the start of each refractory period coincides with a QRS complex or the start of an R-wave. Thus a beat interval RR1 is identified at 174 from the start of one refractory period to the next, and additional intervals RR2 176, RR3 178 and RR4 180 are shown. As shown at 182, cardiac rate in beats per minute (BPM) can be calculated using a "4 RR Average" by dividing the average of RR1, RR2, RR3 and RR4 into 60 seconds. Other methods can be used to calculate rate from a set of R-wave detections, for example, as shown in U.S. Pat. No. 8,909,331, the disclosure of which is incorporated herein by reference.

FIGS. 6 and 7 illustrate, graphically, a second method of determining cardiac beat rate. The method of these Figures corresponds, generally to methods described in U.S. patent applications Ser. Nos. 14/819,817, 14/819,851, and 14/819, 889, the disclosures of which are incorporated herein by reference. In the method illustrated in FIG. 6, a buffer 200 of several second of data is shown with an ECG 202. A comparator 204 is generated using a segment of the ECG 202, for example, the most recent 1-2 seconds of the ECG 202 is used.

This comparator 204 is then compared against the ECG 202 at a number of lag depths. Thus, beginning at a first lag depth of zero, all the peaks and other features of the comparator 204 will align with identical peaks and features of the ECG 202, giving a 100% match between the comparator 204 and the ECG 202. The comparator is repeatedly compared against the ECG at increasing lag depths, for example as illustrated at 212 and 214. As the comparator 204 is scanned across the ECG 202, for example, peak 206 of the comparator will eventually be compared against peak 210 of the ECG, giving a low correlation between the two. Once the peak 206 of the comparator 204 is aligned with peak 208 of the ECG, however, a much higher correlation will be shown.

The comparison results at the lag depths tested are graphed in FIG. 7. The lag depths plotted on the X-axis, and the comparisons are scaled to a range from zero to one on the Y-axis. At a lag depth of zero, the correlation of the comparator and ECG is essentially one, and after that the correlation drops to low values 220 and generally stays there except for when the R-wave peaks align with one another. The result in the plot of FIG. 7 includes several peaks 224, 226, 228 which correspond to lag depths where the R-waves in comparator 204 align with R-waves of the buffer 200.

For example, referring to FIG. 6, when peak 206 and peak 208 are aligned with one another, the plot in FIG. 7 will exhibit a peak 224 at a particular lag depth. The lag depth, in this example, represents the number of samples by which the comparator 204 is shifted to yield peak 224 in the plot on FIG. 7. When a peak 224 appears (possibly subject to testing rules suggested, for example, in U.S. patent application Ser. No. 14/819,851), then a lag depth corresponding to the cardiac rate can be identified. For example, if the sampling rate is 256 Hz, and the lag depth for peak 226 is at 200 samples, the lag depth is about 200 times 4 milliseconds, or 800 milliseconds. A cardiac rate of 75 bpm is calculated by dividing 60 bpm by 800 milliseconds. Confidence in this calculation is generated by observing whether the peaks 224, 226 and 228 appear at regular intervals in the plot of FIG. 7.

In summary, the method of FIGS. 6-7 compares a segment 204 of the cardiac signal 202 to itself at varying degrees of temporal offset (lag depth) to identify a periodicity (indicated by peaks 224 in the plot of FIG. 7) of the cardiac signal and deriving a heart rate (60 bpm divided by the lag depth) therefrom.

It can be seen that the method of FIGS. 6-7 is highly differentiated from the method of FIG. 5. For this reason, the use of these two methods of analysis, if each provides a similar rate output, would likely provide a high confidence that the output rate is correct.

Figure 8:
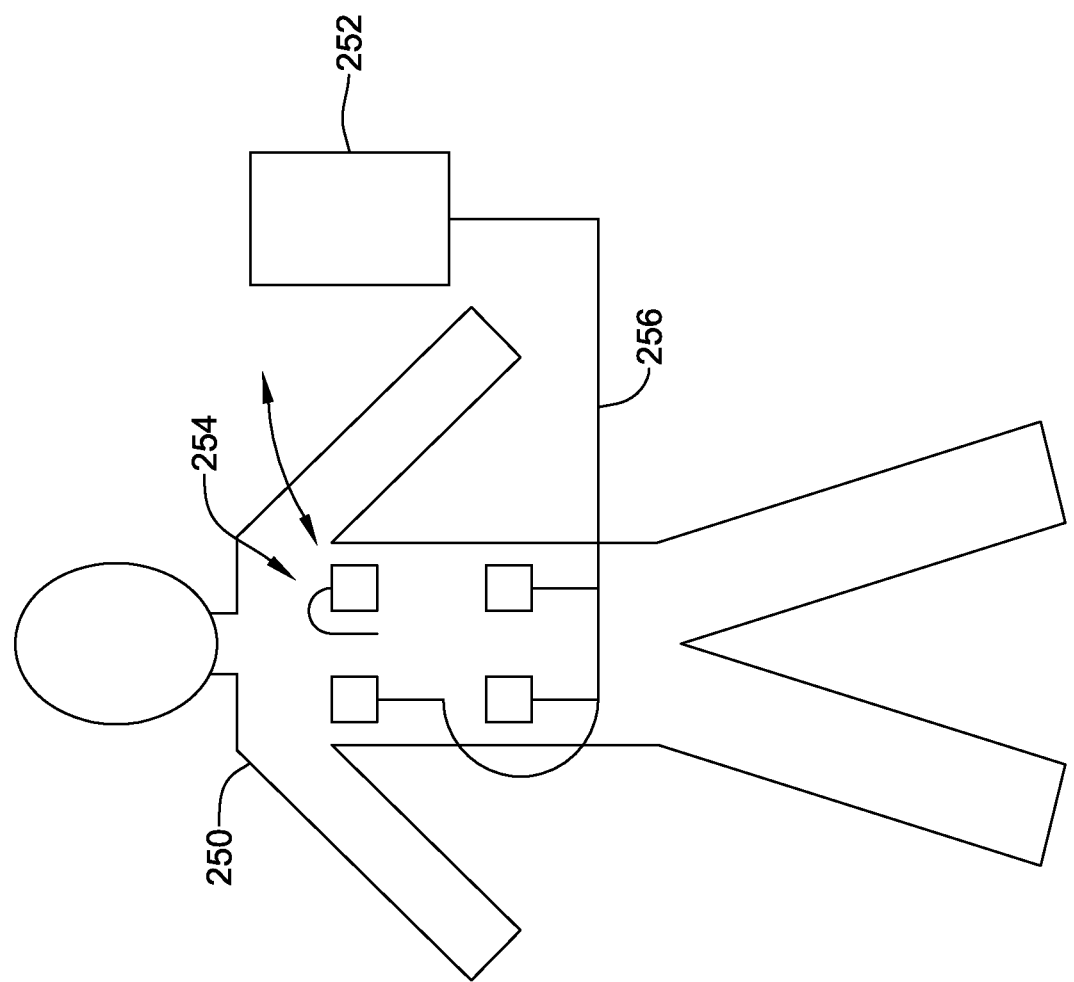
FIGS. 8 and 9 show additional illustrative systems for patient screening.
Figure 9:
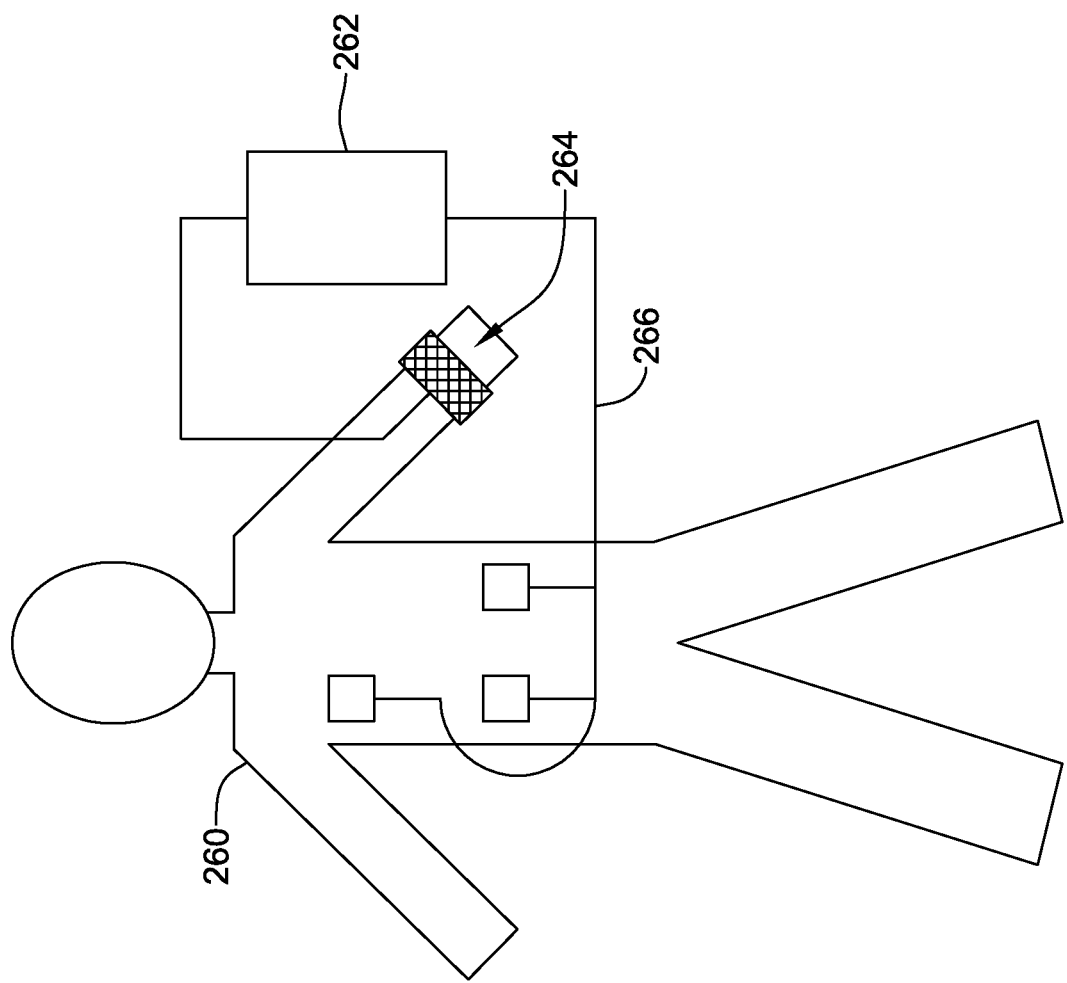

FIGS. 8 and 9 show additional illustrative systems for patient screening. An external device 252 is configured to perform screening on the patient 250 relative to a proposed implantable medical device. In the example of FIG. 8, the patient 250 already has an implantable transvenous system 254 having a lead that is coupled to the heart. Such a device, given its contact with the heart, is likely to be able to provide a very accurate cardiac rate (absent any malfunction). The external device 252 may be configured to communicate with the implanted device 254, for example, using inductive, RF, conducted or other communication techniques, to obtain the heart rate from the implanted device 254. A cutaneous electrode system 256 is also provided to capture surface signals for use in emulating the proposed implantable device operation. If desired, rather than a set of wired electrodes, wireless cutaneous electrodes may be used and would then wirelessly communicate the signals captured by each to the external device 252. In this example, the at least first and second rate (block 132 in FIG. 4) can be generated by taking one rate from the implantable device 254 and the other rate from the cutaneous electrode system 256.

FIG. 9 illustrates another example in which the patient 260 is provided with a cuff 264 for capturing rate, with the cuff 264 coupled to an external device 262. The cuff 264 may be a pressure cuff adapted to sense changing blood pressure to generate a beat rate. In an alternative, the cuff 264 is replaced with a different device such as a pulse oximetry interface for using pulse oximetry to calculate rate. In another alternative, the cuff 264 is replaced with a microphone for capturing heart sounds to generate a beat rate. The external device 262 is also coupled to a cutaneous electrode system 266 for capturing a surface ECG and generating a second cardiac rate. In this example, the at least first and second rate (block 132 in FIG. 4) can be generated by taking one rate from the cuff 264 (or other device, as noted) and the other rate from the cutaneous electrode system 266.

Although each of FIGS. 8 and 9 show an external device which is coupled to both the surface electrodes and a second device, separate devices may be used instead. In addition, the surface or cutaneous electrodes, pressure cuff, or pulse oximeter in any of the above examples may be provided by wireless devices, such that the input/output port of the external device can comprise wireless circuitry, rather than jacks or electrical sockets/ports or plug-ins for coupling to wired electrodes or other device.

Figure 10:
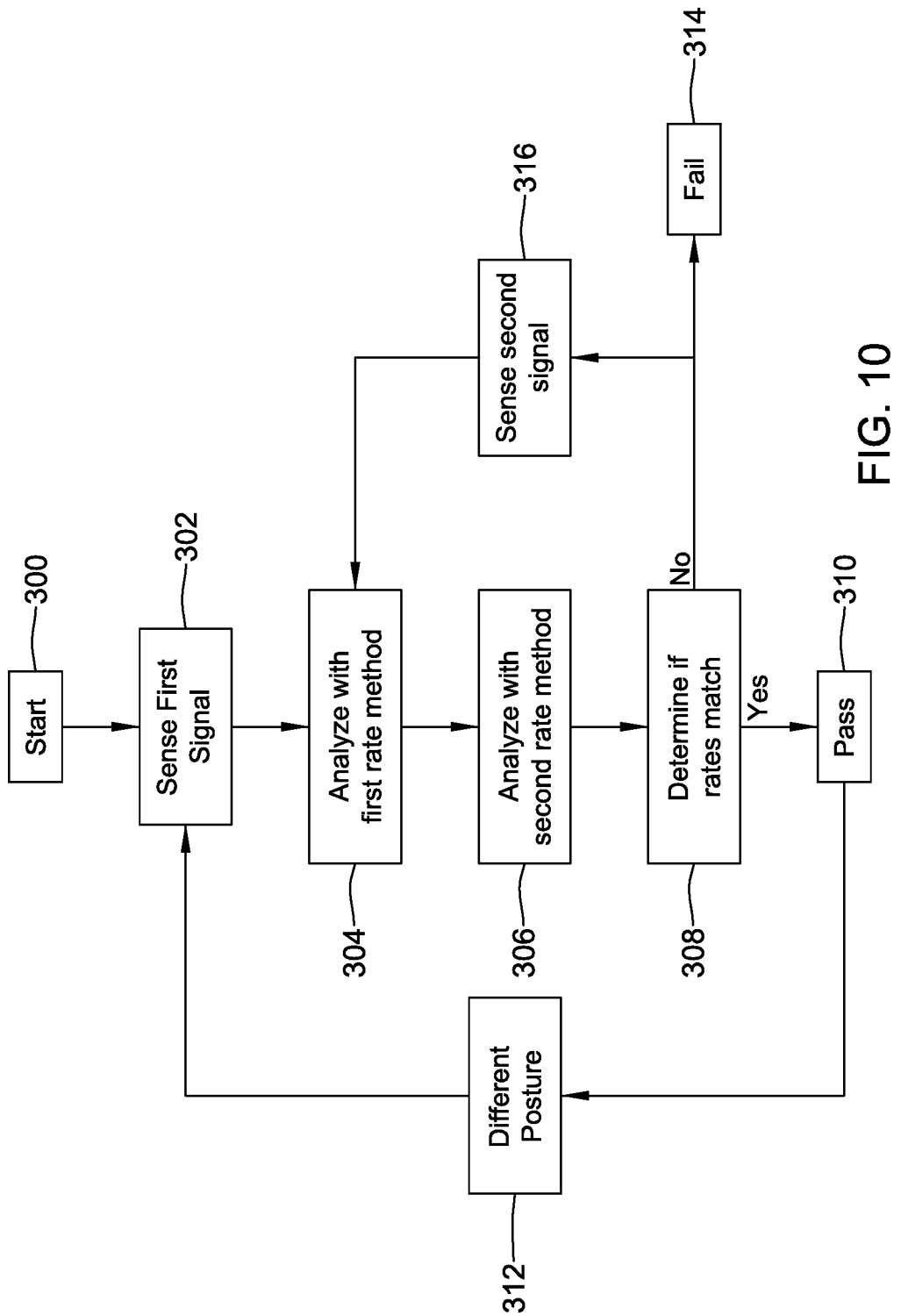
FIG. 10 is a flow diagram for an illustrative method of patient screening.

FIG. 10 is a flow diagram for an illustrative method of patient screening. The illustrative method begins at start block 300 and proceeds to sensing a first signal 302. In an example, the first signal is a cardiac electrical signal that is sensed through the skin using cutaneous electrodes. The first signal may be analyzed with a first rate method, as shown at 304. In an example, the first method at 304 is a beat detection method using comparison of a captured cardiac electrical signal to a threshold. In another example, the first method emulates any method that may be used by an implantable device or system.

Next an analysis is performed with a second rate method, as shown at 306. Examples for the second rate method include analysis of an electrical cardiac signal using a different approach than that of the first method, heart sounds, pulse oximetry, and blood pressure measurements, or a rate calculated by an already implanted medical device. Next, the rates resulting from analysis in blocks 304, 306 are compared to one another, as shown at 308. If a match is found, the patient may pass 310 pre-implant screening for a given implantable medical device. If desired, the method may then be repeated using one or more additional postures 312, for example, with the patient going from seated to standing, seated to laying down on his/her back, or seated to prone, or other combination. Instead of a different posture 312, an exercise analysis may be performed while the patient walks, jogs, or uses an elliptical trainer, for example. Retesting in the different posture or with exercise may then be performed using blocks 302/304/306/308.

If the rates do not match at 308, the patient may fail screening, as indicated at 314. Alternatively, a second signal may be sensed, as indicated at 316. For example, a set of cutaneous electrodes used in testing may be moved to locations corresponding to a different implantable medical device position than those used to sense the first signal at 302. In another example, a different sensing vector among available sensing vectors may be selected for the second signal 316. Retesting can then be performed via blocks 304/306/308.

Figure 11:
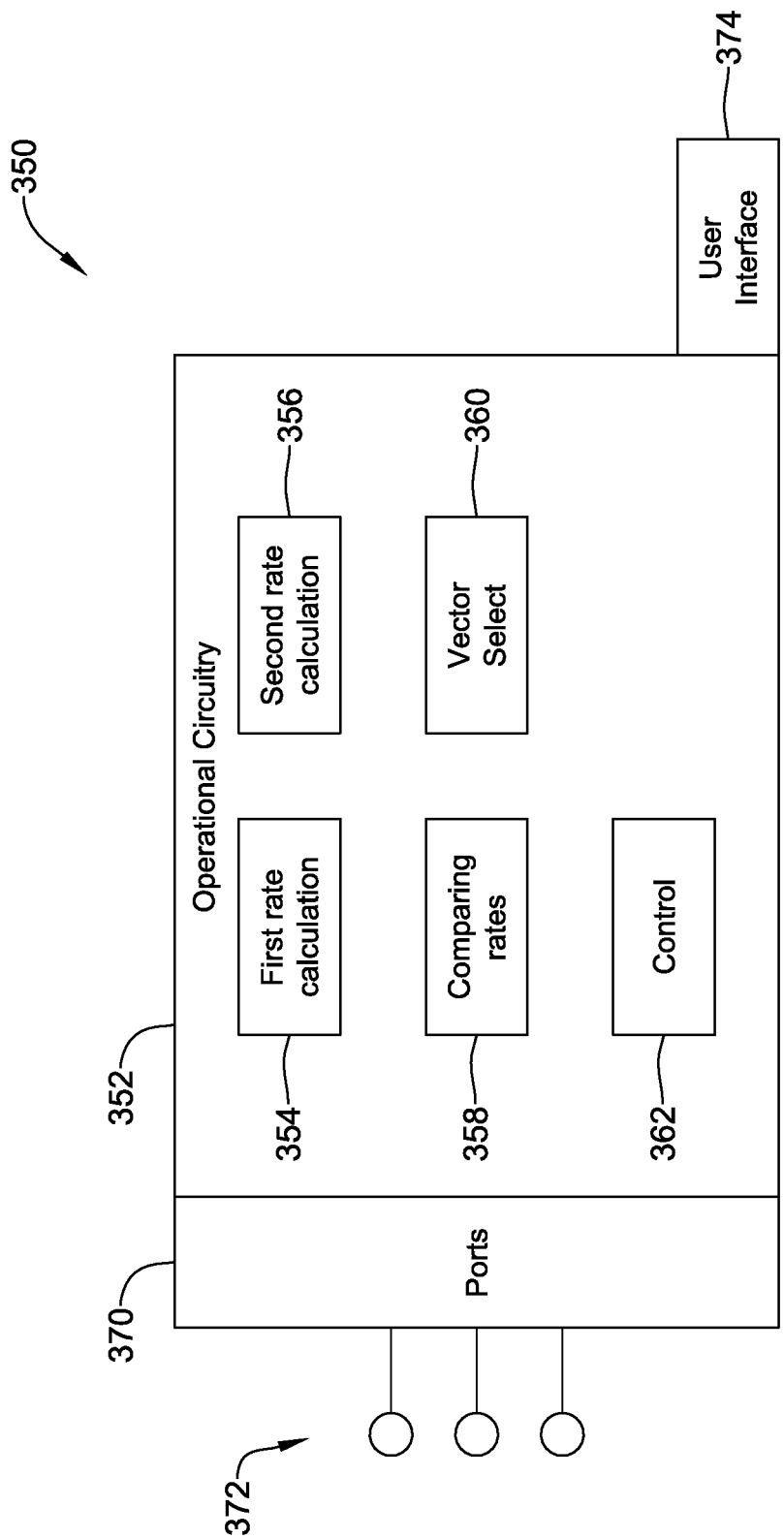
FIG. 11 is a functional block diagram for an illustrative device.

FIG. 11 is a functional block diagram for an illustrative device. The device 350 may be an external programmer having a microcontroller or microprocessor. The device 350 may be a general purpose computer, preferably mobile, such as a laptop computer, or, more preferably, a mobile phone or tablet computer. Alternatively, the device may be a specially designed and purposed medical device.

In any event, the device includes operational circuitry 352 which can perform a number of functions. These functions include performing a first rate calculation 354, a second rate calculation 356, comparing rates 358 from the two rate calculations 354, 356, selecting a vector 360, and an overall control block 362 which facilitates use of signals from a port or set of ports 370 configured for coupling to cutaneous electrodes 372, as well as a user interface 374. The various functional blocks 354, 356, 358, 360, 362 may be implemented in software and can be functional blocks within software or firmware of the device 3550. One or more of the functional blocks 354, 356, 358, 360, 362 may instead be implemented as a set of discrete circuit components or as an application specific integrated circuit.

Though not shown, the device 350 may also include wireless and/or inductive communication circuitry, optical, serial, parallel, and other input/output ports. The user interface may include a touchscreen, a keyboard, a microphone and/or speaker, or any other suitable device for obtaining inputs from a user and/or providing output information or commands to a user. For example, the user interface 374 may include a screen for providing instructions to a user to have a patient adopt one or more postures, or to indicate to the user whether to reposition the cutaneous electrodes 372. Batteries and line power supply circuitry are omitted from the figure as well but would be included as suits a particular design.

A first non-limiting example takes the form of a screening device configured to perform patient screening to determine whether a patient is well suited to receiving a first implantable medical device (IMD) comprising: a user interface (FIG. 11, 374, for example); an port configured to receive signals from at least surface electrodes for cutaneous placement on a patient (FIG. 11, 370, for example); and operational circuitry (such as circuitry and or programming instructions represented in FIG. 11, block 352, for example) configured to receive signals from the port and perform a patient screening method, and to use the user interface to provide information and/or instructions to a user and receive inputs therefrom. In the first non-limiting example, the operational circuitry may comprise first rate calculation means (for example, circuitry or programming instructions represented by functional block 354 of FIG. 11) for calculating a first cardiac rate using signals from the surface electrodes by a first analysis, second rate calculation means (for example, circuitry or programming instructions represented by functional block 356 of FIG. 11) for obtaining a second cardiac rate by a second analysis; wherein the second analysis is different from the first analysis; and comparing means (for example, circuitry or programming instructions represented by functional block 358 of FIG. 11) for comparing the first cardiac rate to the second cardiac rate to determine whether the patient is well suited to receiving the first IMD if the first cardiac rate and the second cardiac rate match within predetermined bounds.

A second non-limiting example takes the form of a screening device as in the first non-limiting example, wherein the first rate calculation means is configured such that the first analysis is similar to an analysis which the first IMD would use to analyze cardiac signals. A third non-limiting example takes the form of a screening device of either of the first two non-limiting examples wherein the comparing means is configured to provide an output via the user interface indicating that the patient is not well suited to receiving the IMD if the first and second rates do not match.

A fourth non-limiting example takes the form of a screening device as in any of the first three non-limiting examples, wherein the first analysis comprises a beat detection method for detecting individual heartbeats by comparison of a signal to a detection threshold, and the second analysis comprises comparing a segment of a signal received from the surface electrodes to itself at varying degrees of temporal offset to identify a periodicity of the signal. A fifth non-limiting example takes the form of a screening device as in any of the first three non-limiting examples, wherein the first analysis comprises a beat detection method for detecting individual heartbeats by comparison of a signal to a detection threshold, and the second analysis comprises obtaining a heart rate from a blood pressure monitoring system communicatively coupled to the screening device. A sixth non-limiting example takes the form of a screening device as in any of the first three non-limiting examples, wherein the first analysis comprises a beat detection method for detecting individual heartbeats by comparison of a signal to a detection threshold, and the second analysis comprises obtaining a heart rate by the use of a pulse oximeter communicatively coupled to the screening device.

A seventh non-limiting example takes the form of a screening device as in any of the first three non-limiting examples, wherein the first analysis comprises a beat detection method for detecting individual heartbeats by comparison of a signal to a detection threshold, and the second analysis comprises obtaining a heart rate by interrogation of an already implanted cardiac management or monitoring system communicatively coupled to the screening device in the patient. An eighth non-limiting example takes the form of a screening device as in any of the first three non-limiting examples, wherein the first analysis comprises a beat detection method for detecting individual heartbeats by comparison of a signal to a detection threshold, and the second analysis comprises obtaining a heart rate by monitoring heart sounds.

A ninth non-limiting example takes the form of a screening device as in any of the first eight non-limiting examples, which is configured to output, via the user interface, a desired posture for the patient to assume during a first assessment by the first and second rate calculation means and which, upon completion of analysis by the first and second rate calculation means, is configured to output, via the user interface, a second desired posture for the patient to assume during a second assessment by the first and second rate calculation means. A tenth non-limiting example takes the form of the ninth non-limiting example, wherein the first posture is seated and the second posture is laying down. An eleventh non-limiting example takes the form of the ninth non-limiting example wherein the first posture is seated and the second posture is prone.

A twelfth non-limiting example takes the form of a screening device as in any of the first eleven non-limiting examples, further configured to indicate, via the user interface, that the patient is to be exercising during a first assessment by the first and second rate calculation means.

A thirteenth non-limiting example takes the form of a system comprising a screening device as in any of the first twelve non-limiting examples further comprising a plurality of cutaneous electrodes (such as electrodes 372 of FIG. 11) configured to couple to the input port of the device. A fourteenth non-limiting example takes the form of a system as in the thirteenth non-limiting example, wherein the operational circuitry further comprises selection means (such as circuitry and/or programming instructions represented by functional block 360 of FIG. 11) for selecting a subset of the cutaneous electrodes for use in analysis by the first and second rate calculation means. A fifteenth non-limiting example takes the form of a system as in the fourteenth non-limiting example, wherein the selection means is configured to select a subset of the cutaneous electrodes for a first iteration of patient assessment by the first and second rate calculation means and a second subset of the cutaneous electrodes for a second iteration of patient assessment by the first and second rate calculation means, to check whether the patient is well suited for receiving the first IMD in light of analysis of each of at least first and second subsets of the cutaneous electrodes.

Each of these non-limiting examples can stand on its own, or can be combined in various permutations or combinations with one or more of the other examples.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic or optical disks, magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description.

The Abstract is provided to comply with 37 C.F.R. § 1.72(b), to allow the reader to quickly ascertain the nature of the technical disclosure. It is submitted with the understanding that it will not be used to interpret or limit the scope or meaning of the claims.

Also, in the above Detailed Description, various features may be grouped together to streamline the disclosure. This should not be interpreted as intending that an unclaimed disclosed feature is essential to any claim. Rather, inventive subject matter may lie in less than all features of a particular The claimed invention is:

1. A screening device configured to perform patient screening to determine whether a patient is well suited to receiving a first implantable medical device (IMD) comprising:
   a user interface;
   a port configured to receive signals from at least surface electrodes for cutaneous placement on a patient; and
   operational circuitry configured to receive signals from the port and perform a patient screening method, and to use the user interface to provide information and/or instructions to a user and receive inputs therefrom;
   wherein the operational circuitry is configured to:
   perform a first method of determining cardiac rate using signals from the surface electrodes to calculate a first cardiac rate, wherein the first method is similar to a method used by the first IMD to determine cardiac rate;
   obtain a second cardiac rate by a second method different from the first method; and
   compare the first cardiac rate to the second cardiac rate and determine whether the first cardiac rate and second cardiac rate are similar, and, if so, determine that the patient is well suited to receiving the first IMD.

2. A system comprising the screening device of claim 1 and a plurality of cutaneous electrodes communicatively coupled to the port of the device, wherein the operational circuitry of the screening device is configured such that:
   the first cardiac rate is calculated using a first pair of the cutaneous electrodes that define a first sensing vector, if the first rate and the second rate do not match using the predefined parameters, the operational circuitry is configured to select a different pair of the cutaneous electrodes that define a second sensing vector and repeat the steps of calculating a first cardiac rate, this time using the second sensing vector in order to determine whether the second sensing vector yields a match of the first and second cardiac rates.

3. The screening device of claim 1 wherein the operational circuitry is configured such that the first method for generating a heart rate comprises a beat detection method for detecting individual heartbeats by comparing a signal to a detection threshold, and the second method for generating a heart rate comprises comparing a segment of a signal to itself at varying degrees of temporal offset to identify a periodicity.

4. The screening device of claim 1 wherein the operational circuitry is configured such that the first method for generating a heart rate comprises a beat detection method for detecting individual heartbeats by comparing a signal to a detection threshold, and the second method for generating a heart rate comprises the use of a pressure monitoring system communicatively coupled to the screening device.

5. The screening device of claim 1 wherein the operational circuitry is configured such that the first method for generating a heart rate comprises a beat detection method for detecting individual heartbeats by comparing a signal to a detection threshold, and the second method for generating a heart rate comprises the use of a pulse oximeter communicatively coupled to the screening device.

6. The screening device of claim 1 wherein the operational circuitry is configured such that the first method for generating a heart rate comprises a beat detection method for detecting individual heartbeats by comparing a signal to a detection threshold, and the second method for generating a heart rate comprises interrogation of an already implanted cardiac management or monitoring system communicatively coupled to the screening device.

7. The screening device of claim 1 wherein the operational circuitry is configured such that the first method for generating a heart rate comprises a beat detection method for detecting individual heartbeats by comparing a signal to a detection threshold, and the second method for generating a heart rate comprises the use of heart sounds.

8. An external device for use in assessing a patient's suitability for receiving an implantable cardiac device comprising:
   a user interface for providing instructions and information to and receiving inputs from a user;
   a first means for detecting cardiac rate, the first means providing a cardiac rate that is configured to emulate a cardiac rate that would be calculated by an implantable medical device;
   a second means for detecting cardiac rate, the second means providing a cardiac rate that is configured to be more accurate than the first means; and
   a controller for comparing the cardiac rates of the first and second means and directing the inputs and outputs of the user interface.

9. The external device of claim 8 further comprising a port configured to receive signals from at least surface electrodes for cutaneous placement on a patient; wherein each of the first means for detecting cardiac rate and the second means for detecting cardiac rate are coupled to the port, and the first means for detecting cardiac rate is configured to use a beat detection method comprising comparing cardiac electrical signals to a detection threshold to identify cardiac cycles and thereby determine heart rate, and the second means for detecting cardiac rate is configured to comparing a segment of a signal obtained from the port to itself at varying degrees of temporal offset to identify a periodicity.

10. The external device of claim 8 further comprising a port configured to receive signals from at least surface electrodes for cutaneous placement on a patient; wherein the first means for detecting cardiac rate is coupled to the port to obtain electrical signals from the port indicative of cardiac signals of a patient from which to determine cardiac rate; and the second means for detecting cardiac rate is a blood pressure monitoring system.

11. The external device of claim 8 further comprising a port configured to receive signals from at least surface electrodes for cutaneous placement on a patient; wherein the first means for detecting cardiac rate is coupled to the port to obtain electrical signals from the port indicative of cardiac signals of a patient from which to determine cardiac rate; and the second means for detecting cardiac rate is a pulse oximeter.

12. The external device of claim 8 further comprising a port configured to receive signals from at least surface electrodes for cutaneous placement on a patient; wherein the first means for detecting cardiac rate is coupled to the port to obtain electrical signals from the port indicative of cardiac signals of a patient from which to determine cardiac rate; and the second means for detecting cardiac rate is a communication circuit for communicating with an implanted medical device already in a patient to obtain heart rate thereform.

13. The external device of claim 8 further comprising a port configured to receive signals from at least surface electrodes for cutaneous placement on a patient; wherein the first means for detecting cardiac rate is coupled to the port to obtain electrical signals from the port indicative of cardiac signals of a patient from which to determine cardiac rate; and the second means for detecting cardiac rate is a heart sound sensor for determining heart rate by the use of heart sounds.

\* \* \* \* \*